(12) United States Patent
Senn et al.

(10) Patent No.: US 10,502,939 B2
(45) Date of Patent: Dec. 10, 2019

(54) HOMOGENIZER COMPRISING A LIGHT SOURCE

(71) Applicant: Ivoclar Vivadent AG, Schaan (LI)

(72) Inventors: Bruno Senn, Gais (CH); Markus Pauler, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 16/061,173

(22) PCT Filed: Dec. 15, 2016

(86) PCT No.: PCT/EP2016/081163
§ 371 (c)(1),
(2) Date: Jun. 11, 2018

(87) PCT Pub. No.: WO2017/102933
PCT Pub. Date: Jun. 22, 2017

(65) Prior Publication Data
US 2018/0364464 A1 Dec. 20, 2018

(30) Foreign Application Priority Data
Dec. 16, 2015 (EP) ..................................... 15200486

(51) Int. Cl.
| G02B 19/00 | (2006.01) |
| A61C 13/15 | (2006.01) |
| F21V 8/00 | (2006.01) |
| G02B 27/09 | (2006.01) |
| A61B 1/06 | (2006.01) |
| F21Y 115/10 | (2016.01) |

(52) U.S. Cl.
CPC ............ *G02B 19/0028* (2013.01); *A61B 1/06* (2013.01); *A61C 19/003* (2013.01); *G02B 6/0008* (2013.01); *G02B 27/0977* (2013.01); *G02B 27/0994* (2013.01); *F21Y 2115/10* (2016.08); *G02B 6/0096* (2013.01)

(58) Field of Classification Search
CPC ............ G02B 19/0028; G02B 19/0061; G02B 19/0019; G02B 27/0994; G02B 27/0977; G02B 6/0008; G02B 6/0096; A61B 1/06; A61C 19/003; F21Y 2115/10
See application file for complete search history.

(56) References Cited

U.S. PATENT DOCUMENTS

| 5,223,986 A | 6/1993 | Mayerjak et al. |
| 6,863,418 B2 | 3/2005 | Masuoka et al. |
| 2004/0021853 A1* | 2/2004 | Stam ................... B60Q 1/1423 356/218 |
| 2004/0029069 A1 | 2/2004 | Gill et al. |

(Continued)

FOREIGN PATENT DOCUMENTS

| JP | 2007-66911 A | 3/2007 |
| JP | 2008-235207 A | 10/2008 |

*Primary Examiner* — Victor A Mandala
(74) *Attorney, Agent, or Firm* — Ann M. Knab; Thad McMurray

(57) ABSTRACT

The invention relates to a homogenizer having an input surface and an output surface which are incongruent to one another, at least one inclined surface extending between the input surface and the output surface. The inclined surface is corrugated. According to the invention, the homogenizer is designed as a hollow element which surrounds the LED chips (14) reflectively.

19 Claims, 8 Drawing Sheets

(56) References Cited

U.S. PATENT DOCUMENTS

| | | | |
|---|---|---|---|
| 2006/0251376 A1* | 11/2006 | Cianciotto | G02B 6/0096 |
| | | | 385/146 |
| 2007/0001177 A1 | 1/2007 | Bruning et al. | |
| 2007/0024971 A1* | 2/2007 | Cassarly | G02B 6/0008 |
| | | | 359/485.03 |
| 2008/0093530 A1 | 4/2008 | Hoelen et al. | |
| 2009/0001490 A1 | 1/2009 | Bogner et al. | |
| 2010/0140450 A1 | 6/2010 | Duret et al. | |
| 2010/0142208 A1* | 6/2010 | Kokado | F21V 7/0066 |
| | | | 362/296.07 |
| 2011/0248187 A1 | 10/2011 | Wang et al. | |
| 2012/0236559 A1 | 9/2012 | Sachsenweger et al. | |
| 2013/0027696 A1* | 1/2013 | Sekiyama | G01J 3/513 |
| | | | 356/300 |
| 2013/0094210 A1 | 4/2013 | Rice et al. | |
| 2016/0290597 A1 | 10/2016 | Jurik et al. | |
| 2016/0298813 A1* | 10/2016 | Jurik | F21V 11/186 |

* cited by examiner

HOMOGENIZER COMPRISING A LIGHT SOURCE

CROSS-REFERENCE TO RELATED APPLICATIONS

This application is a National Stage application of International patent application PCT/EP2016/081163 filed on Dec. 16, 2016, which claims priority to European patent application No. 15200486.7 filed on Dec. 16, 2015, the disclosures of which are incorporated herein by reference in their entirety.

FIELD OF THE INVENTION

The invention relates to a homogeniser, and more particularly to a light curing apparatus having a homogeniser.

BACKGROUND OF THE INVENTION

In light curing apparatuses, especially for dental purposes, it has been known for long to use an optical fiber, to guide the light originating from the light source to the treatment site. The optical fiber may be formed as a light guide rod or as a light fiber rod, or also as a combination thereof.

Typically, as light sources, LED chips but also laser chips are used, which each emit a predetermined wavelength spectrum, and exciting the intermixed photo initiator, for example camphor chinone, in the dental restauration material that is to be hardened, to assure polymerization.

It is especially important for the polymerization to occur consistently. While, in dental restoration parts being located in a depth of some millimeters an appropriately longer polymerization time is selected, to also assure polymerization of the underlying regions, it is important for the polymerization to consistently occur even in horizontal direction, i.e. in a direction transversally to the emission axis of the light guide rod. Typically, the light emitted by the light source is collected, as it is known for example from U.S. Pat. No. 4,742,432 A1. Center-focusing and focusing of the emitted light beam will arise from this. Said center-focusing may not readily be seen with the naked eye, and thus the dentist relies on the light emission to consistently occur across the entire emissions area, for example in a circle diameter of 1 cm, even if this is not the case due to the center-focusing.

To counteract center-focusing and inconsistent illumination, it has been known for long to interpose mixing elements between the light guide rod or light fiber rod on the one hand and the light source on the other hand. As light mixing elements, for example glass elements comprising reflecting mini elements, which are evenly distributed in the glass elements, are used. Opacification of the glass element or other transparent element may be used to assure homogenization and diffusion.

Moreover, arrangement of ribs on the outside of the light mixing element has also be proposed, which essentially extend in the longitudinal direction of the light mixing element, i.e. essentially parallel to the direction of light. Depending on the rib angle, said longitudinal ribs create different reflections, especially due to the different diffraction indices between the surrounding air and the light mixing elements consisting of glass or other transparent plastic material.

It has also been proposed to metallize the ribs of the glass-mixing element by vapor deposition of a mirror layer, thus improving reflection effect.

Typically, the LED chips are arranged to have rectangular outer dimensions, or even are square in shape.

On the other hand, many different forms of the LED chip arrangement may be utilized depending on the desired power and configuration of the light curing apparatus, so that for optimum light mixing, different light mixing elements are required to be provided.

Moreover, light guide rods having diameters of 8 mm and 10 mm are provided. Accordingly, on the output side, provision of different light exit surfaces are to be taken into account, to assure loss-free light conduction, thus doubling the number of light mixing elements being required.

Moreover, rib mixer have already become known as homogenisers having different input and output forms. Such homogenisers typically comprise an input surface and an output surface auf and are filled with transparent material. Alternatively, they may also be formed as hollow elements. Said hollow elements suffer from the additional expenses and optical losses, which are generated by such a homogeniser as an ancillary part, so that such homogenisers, as a general rule, will not be employed.

SUMMARY OF THE INVENTION

The object of the invention thus resides in the provision of a homogeniser or a light curing apparatus according to the attached claims, which is being optimized in regard of light output and homogenization of the light emission on the one hand, but also in regard of storage costs on the other hand.

This object will be solved by the Claim 1 or 15, respectively. Advantageous embodiments will arise from the Sub-claims.

According to the invention, the light mixing element or homogeniser is provided comprising corrugation, which extends in a known manner from the input surface to the output surface. The homogeniser according to the invention is formed as a hollow element. In the interior, air or another gas, or a vacuum, if required, is provided.

According to the invention, it is especially beneficial for the homogeniser to surround the light source. After the homogeniser having been formed as a reflecting hollow element, it will reflect the light emitted by the light source, so that the homogeniser simultaneously acts as a main reflector for the light source.

Additional effort for the provision of a separate homogeniser will thus be eliminated, and the hollow element according to the invention is dual-functional, which surprisingly represents significant progress compared to the solutions known so far.

It is preferred for the homogeniser to be sealed with a transparent plate at the output surface. It is preferred for the hollow element of the homogeniser to abut against a base plate with its input-side front face, which extends parallel to the input surface and onto which, in addition, the LED chips of the light source are mounted. Herein, sealing may readily be accomplished. The interior space of the hollow body is sealed, preventing pollutants to be able to occur.

According to the invention, the homogeniser is an element comprising corrugation, which extends around the outer circumference. Thus, the wall of the hollow body is not straight, but is corrugated across the entire circumference. In one embodiment, deformation is beneficial, so that, with the hollow element according to the invention all input-side and output-side configurations may surprisingly be covered in praxis.

In a modified embodiment, the homogeniser is formed as a solid body, which on the outside is preferably formed essentially cylindrical, and is essentially truncated in the interior. In this embodiment, a two-part or multi-part realization of the homogeniser is reasonable, or is even required, to facilitate mounting onto the base plate.

It is to be understood, that in this case, on the outside of the cylindrical outer surface of the homogeniser the snap-lock fasteners may be formed, breaking the cylindricity.

Moreover, the embodiment, which is formed as a solid body, has the advantage that heat dissipation of the LED chips is improved, wherein, on the outside of the homogeniser element, cooling ribs may also be provided.

In order to realize diameter reduction of 10 mm to 8 mm at the output surface, the hollow element, with its corrugated interior wall, will briefly be inserted into the respective receiving socket for the 8 mm-light guide rod, which extends away therefrom. The corrugated wall is elastic, such that it adapts, also simultaneously maintaining uniformity of the corrugation due to its elasticity. In this case, the rib angle is somewhat smaller, which, however, does not counteract to the homogenization effect.

According to the invention, even on the input side, the wall of the homogenisier's hollow element may be deformed, if required, so that even with different mounting the LED chips into the ready-to-use light curing apparatus optimum adaption may be realized. Automatic shape adaption at the input side and the output side of the according to the invention hollow element may similarly be realized.

Moreover, in the embodiment according to the invention for the hollow element, transition from squared to circular shape is being automatically set. Typically, the input surface is squared or polygonal and the output surface is of round shape. This automatically results in inclination of the walls of the hollow element, which also is beneficial to multireflection and mixing of the light introduced.

As far as collecting lenses especially on the input side of the homogeniser are provide, they, for example, will be realized as planar-convex lenses.

By way of the corrugation with the angular ribs almost loss-free or at least low-loss homogenization of the introduced light beam occurs.

The light that has been introduced will be reflected at the inclined angles, at which it comes in and will always be reflected several times, which is beneficial to the scattering action.

In another preferred embodiment, it is provided for the hollow element to be formed of two half-shells. Said half-shells may be connected to each other via a snap-lock connection, so that they form an annular hollow reflector, as seen in the cross section.

Instead of this, the groove reflector according to the invention may also be composed of any plurality of segments. It is preferred for the reflector to be of polycarbonate having high surface quality and has a coating comprising a reflecting aluminum layer as well as an additional protective layer thereon.

The input side or input surface of the reflecting hollow element may have any form, adapted to the LED chips used—and eventually casted. Typically, the envelope curve of the casted LED chips is at least polygonal, and the hollow element thereon may be in close proximity to the casted chips applied in SMD technology. Typically, the casting compound of the LED chips forms a respective collecting lense.

The LED chips spaced apart from each other, at least partially have different emission maxima. They are, at least partially, non-coaxially arranged to the optical axis of the input side of the light guide rod. This result in asymmetrical introduction of light in at least one color into the homogeniser. Due to the multireflection at the multi-axes inclined ribs of the reflecting hollow element according to the invention, the emitted light beam reciprocatingly travels in the hollow element as it is reflected several times, until it exits the hollow element.

It is thus especially beneficial for the LED chips to be arranged within the hollow element operating as a reflector. The emitted radiation is completely reflected, and is reflected in inclined angles and several times, which is beneficial to homogenization.

It is thus beneficial for the homogeniser according to the invention to be formed as an internally reflecting hollow.

While in a fixedly mounted light guide rod an additional cover plate may be omitted on the output side of the homogeniser, it is beneficial to provide a transparent cover plate, especially if the light guide rod is replaceable. It is also possible, to realize a moderately resilient coupling which in this case fits the 8 mm light guide rods as well as the 10 mm light guide rods.

The ribs of the corrugation may have any suitable course. A saw tooth shape or triangular shape of the profile the ribs has been proven to be especially beneficial in processing. It may also be beneficial to realize the ribs or corrugation as not having a regular shape, for example a triangular shape or a sinus shape with constant period, but to be irregular, so that incident light beams are reflected in any undefined manner.

While it is preferred for the ribs to be extended in constant manner from the input surface to the output surface, it may also be beneficial in a modified embodiment, to change the height and/or width of at least one part of the ribs across the course from the input surface to the output surface.

According to an advantageous embodiment of the invention, it is provided for the circumference of the input surface and the output surface to be equal to each other.

According to an advantageous embodiment of the invention, it is provided for ribs of the corrugation to continuously extend throughout the input surface to the output surface.

According to an advantageous embodiment of the invention, it is provided for the ribs of the corrugation to taper, as seen from a radially inward direction of the homogeniser.

According to an advantageous embodiment of the invention it is provided for the ribs of the corrugation, as seen from a radially inward direction, to become round, especially with a radius of less than one third, preferably about one sixth of its distance from each other and/or their height.

According to an advantageous embodiment of the invention, it is provided for the ribs to have inclined surfaces, and the inclined surfaces of ribs adjacent to each other having an angle to each other between 60 and 110 degree, preferably over 80 degree.

According to an advantageous embodiment of the invention, it is provided for the ribs, as seen in section, to have an essentially sinusoidal course.

BRIEF DESCRIPTION OF THE DRAWINGS

Further advantages, details and features will result from the following description of several working examples of the invention by way of the drawings, wherein.

DETAILED DESCRIPTION

Figure 1:
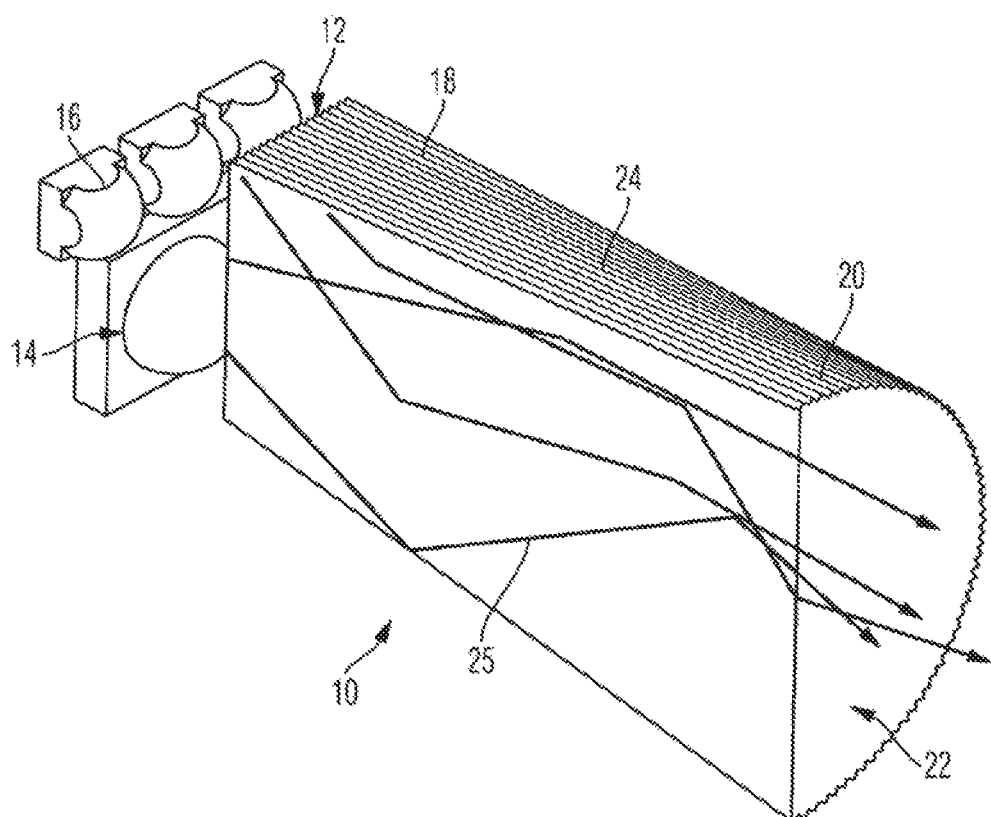
FIG. 1 is a schematic exemplary arrangement of a cut-away homogeniser comprising adjacently arranged LED chips.

From FIG. 1, an exemplary homogeniser 10 as part of a light curing apparatus may be seen. Adjacent to an input surface 12 of the homogeniser 10, a plurality of LED chips 14 are arranged, which each are individually cast with a transparent casting compound 16 to form collecting lenses. In this working example, the cast LED chips 14 are spaced apart from the input surface. The input surface 12 is about squared, wherein in FIG. 1 a rectangular shape is represented, after the homogeniser 10 is represented as being cut-away.

The homogeniser 10 is formed as a hollow element, comprising a corrugation 18 at its outer circumference. The corrugation 18 consists of a multitude of ribs 20, which are evenly distributed across the circumference. The ribs 20 extend, in the course of the homogeniser, along the outer circumference, i.e. from the input surface 12 to an output surface 22.

In the working example represented, the ribs 20 are formed as triangular ribs. The material forming the entire wall 24 of the homogeniser 10 is corrugated, the wall 22 thus being corrugated both inside and outside.

The wall 24 furthermore is provided with a mirror layer in the inside. The mirror layer may for example be realized by a vapor-deposited aluminum layer. To this, preferably a protective layer is applied, to assure constantly good reflection characteristics.

The hollow element or homogeniser 10, with its wall 24, consists of polycarbonate having high surface quality and low roughness at least on the inside.

In the working example represented, the output surface 22 is circular. This is suitable to supply light to the input terminal of a non-represented optical fibers. The input terminal of the optical fiber has exactly the same area as the output surface 22, with at most few percent of deviations. Thus, practically complete light transfer from the homogeniser 10 to the optical fiber is assured.

In FIG. 1, light beams 25 are schematically represented, extending in a multiple reflected manner through the homogeniser 10. What is especially important is the inclined reflection at the ribs 20 on the interior side, resulting in an asymmetric and thus uncontrolled course of the light beams 25 and providing the desired homogenization.

Figure 2:
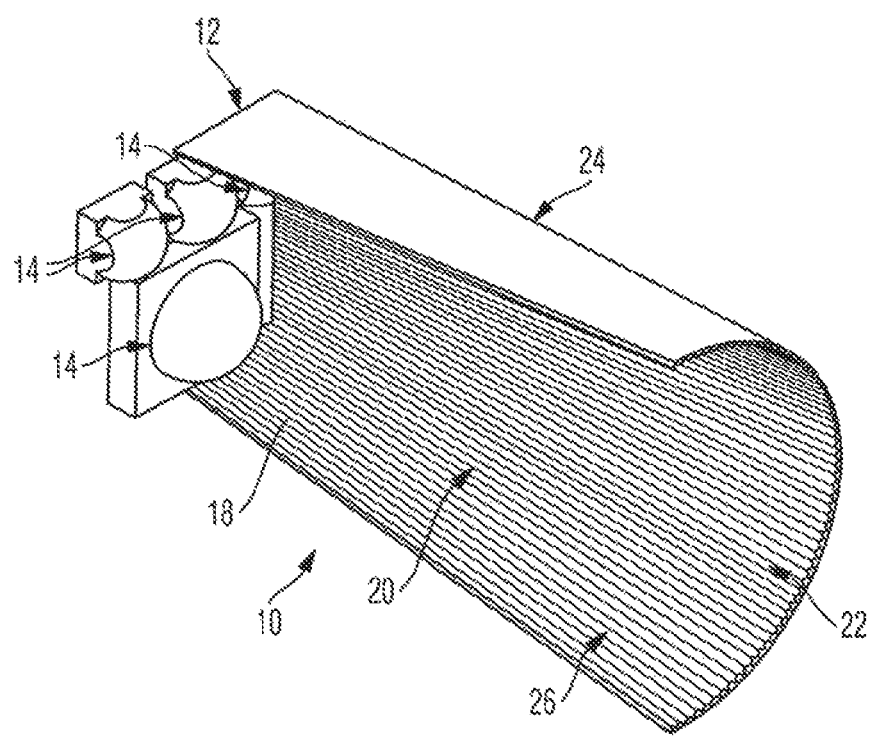
FIG. 2 is an embodiment according to the invention of the homogeniser according to the invention, wherein the LED chips are located in the homogeniser.

In FIG. 2, an embodiment of a homogeniser according to the invention is represented. In this embodiment, the input surface 12 is formed as a rectangular envelope curve for the LED chips 14. It is meant herewith, that the homogeniser, with the inner side of the wall 24, surrounds the multiple arrangement of LED chips 14, and comparatively closely adjacent. In this embodiment, four LED chips 14 are provided, which are symmetrically arranged. In the sectional representation, only two LED chips 14 may be seen from FIG. 7. The input surface 12 extends around the LED chips 14 and preferably such that it comparably closely abuts to the outsides of the LED chips 14.

The LED chips 14 are thus accommodated in the homogeniser 10. With this embodiment, it is assured for all emitted light to be immediately guided into the homogeniser 10 and it is very likely to reflect at the ribs 20 and to be asymmetrically deflected.

In the embodiment represented in FIG. 2 the wall 24 is realized from curved polycarbonate sheet welded as a tube. On the outside, the wall 24 is smooth, whereas it forms a corrugated reflector in the inside.

The output surface, in turn, is circular. It has the same circumference length as the input surface 12. By way of the incongruence in shape, inclined lateral surfaces of the reflector 26, in addition to the inclination of the ribs 20 will be developed. The multi-axial inclination of the reflector 26 and the corrugation 18 support improvement of the homogeniser yields.

Figure 3:
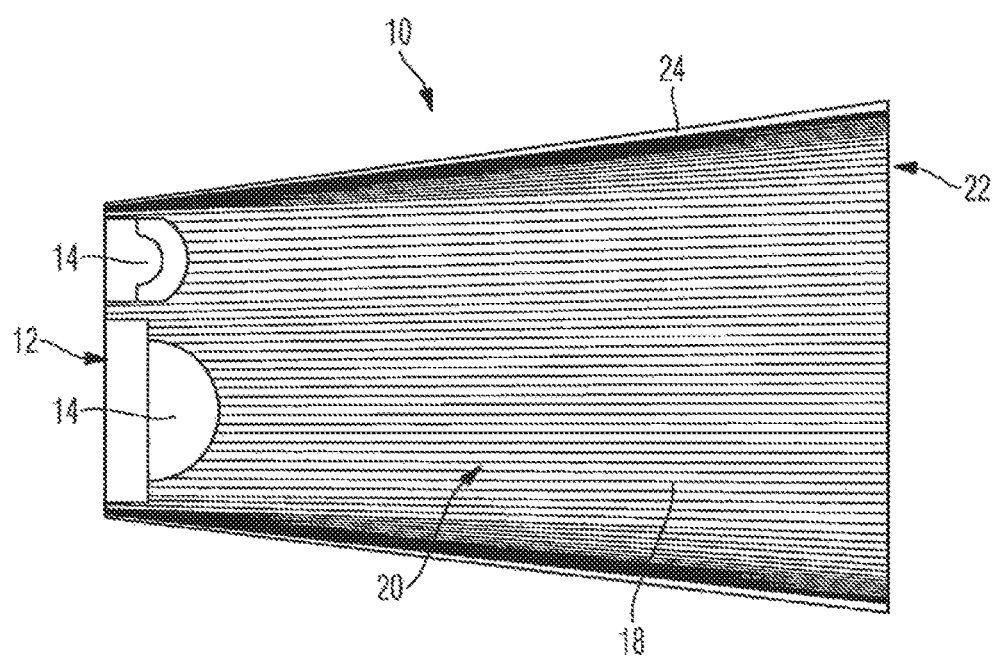
FIG. 3 is a section according to the embodiment of FIG. 2.

The embodiment of the homogeniser according to FIG. 2 is sectionally represented in FIG. 3. Equal reference numbers herein, as in the other figures, will refer to equal or equivalent parts. From FIG. 3, extension of the corrugation perpendicular to both the input surface 12 and the output surface 22 may clearly be seen. It may also be seen, that the surrounding wall 24 extends angularly, thus matching the input surface to the output surface.

Figure 4:
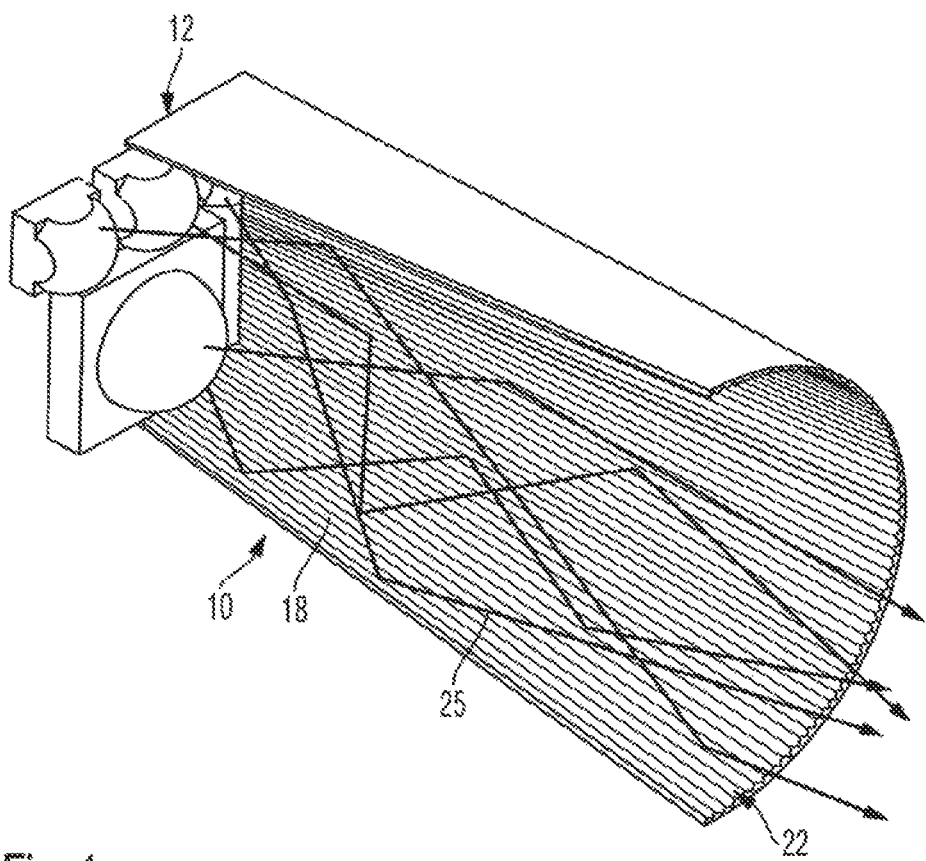
FIG. 4 is another view of the embodiment according to FIGS. 2 and 3.

The embodiment in FIG. 4 corresponds to the embodiment represented in FIG. 2. Additionally, it may be seen, in which way the light beams 25 will be reflected several times and extending from the input surface 12 in the direction to the output surface 22 by being deflected several times under reflection at the corrugation 18.

The FIG. 5A to 5D show different possible forms of the input surface 12, which include the LED chips 14. The wall 24 and thus the reflecting hollow element 10 each extend along the straight outer sides of the cast LED chips 14. It runs obliquely between corners adjacent to each other, but offset to each other, so that the envelope curve around the cast LED chips is closely adjacent thereto.

Figure 5A:
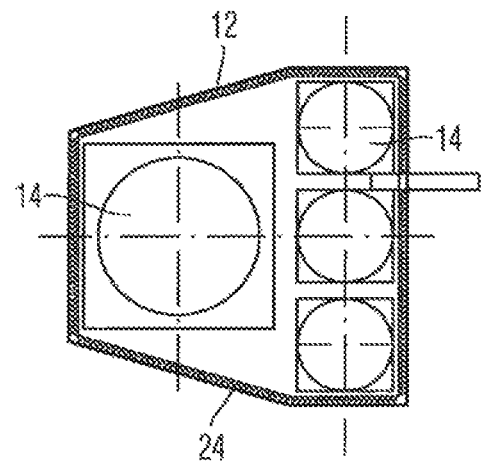
FIG. 5A to 5D are different possible LED arrangements for use with a homogeniser according to the invention.

From FIG. 5A an arrangement of three LED chips 14 having equal wavelength and in one row may be seen. Spaced apart therefrom, but centrally-symmetrically arranged thereto, another larger cast LED chip is provided, which also is surrounded by the wall 24.

The wall 24 according to FIG. 5A is hexagonal in shape.

Figure 5B:
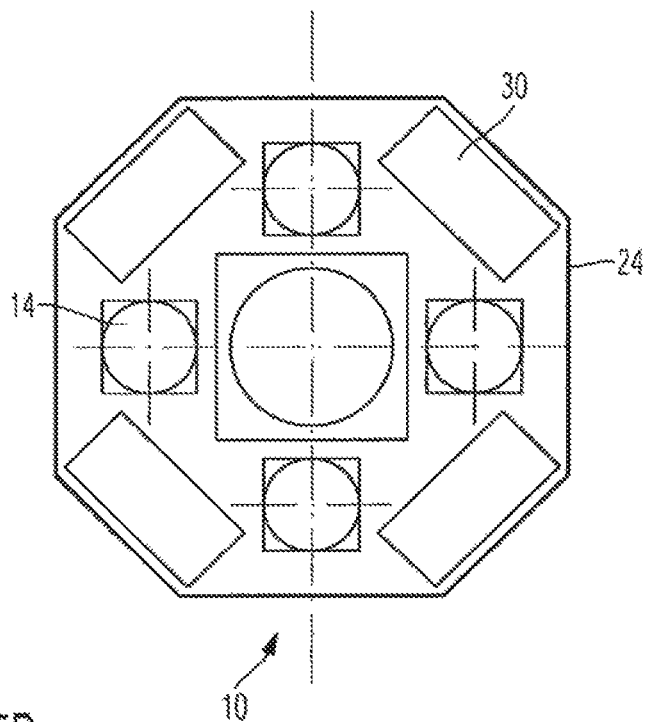

FIG. 5B shows an arrangement von LED chips 14, which are cast, and, in addition, sensors 30 distributed in the gaps therebetween at the outer circumference. The sensors 30 are to acquire light beams in a manner known per se, which are reflected from the surface of the respective material, for example dental material. In the represented embodiment, the sensors 30 are as well surrounded by the wall 24.

In a modified embodiment, it is provided for the sensors 30 to be exempted from homogenization, and to extend the wall 24 within the sensors, but exterior of the LED chips 14. At the locations where sensors 30 are to be found, the wall 24 in this case may be somewhat indented.

This embodiment is especially beneficial in a case, where the reflected light is to be acquired during the light emission of the LED chips, i.e. simultaneously and not during pulse pauses.

Figure 5C:
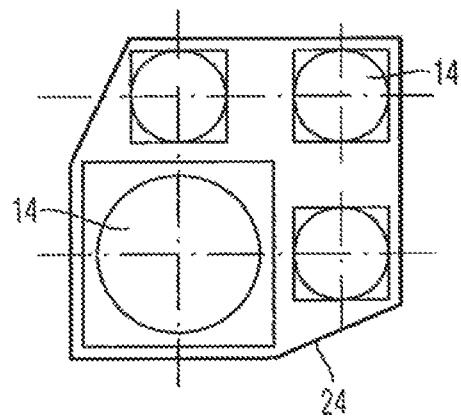

From FIG. 5C, an asymmetric arrangement of the LED chips may be seen. Three LED chips 14 extend laterally beside to or diagonally offset to, respectively, a larger cast LED chip 14. The wall 24 of the homogeniser 10, in turn, extends in an entwinement as short as possible around the LED chips 14.

Figure 5D:
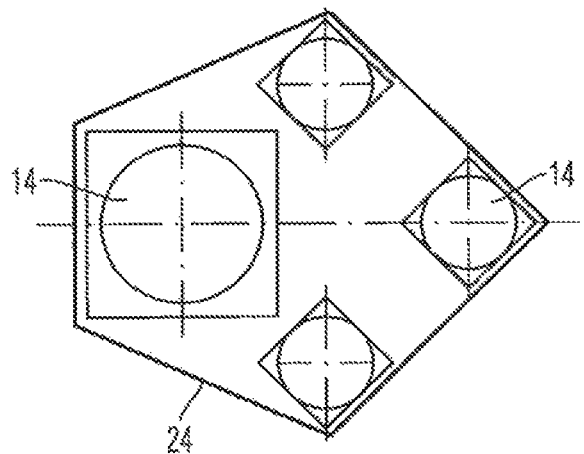

From FIG. 5D, another embodiment of the arrangement of the LED chips 14 may be seen. Three LED chips 14 with a smaller casting compound extend in a triangle, and adjacent to the hypotenuse, an LED chip 14 extends, having a larger casting compound.

In this case, a pentagonal arrangement of the wall 24 results, which surrounds all LED chips 14.

Figure 6A:
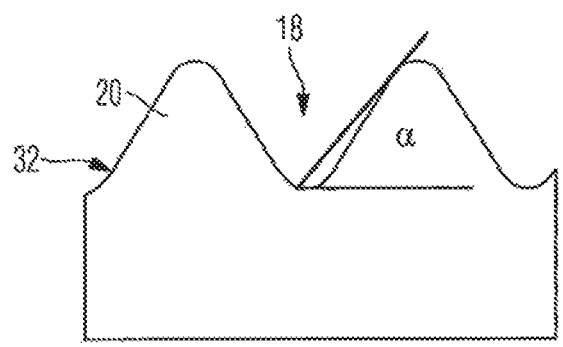
FIG. 6A to 6C are possible forms of the internal reflectors of the homogeniser according to the invention.

From FIG. 6, two exemplary possible forms of the corrugation 18 may be seen. According to FIG. 6A, the corrugation—and thus the ribs 20—extend essentially in sinusoidal manner. A flank 32 of the rib 20 has an angle of inclination of about 45 degrees. This angle simultaneously results from the ratio of dC and dH, i.e. the period and the rib height according to FIG. 6. Both parameters may be constant, or may change around the circumference of the inner corrugation 18.

Figure 6B:
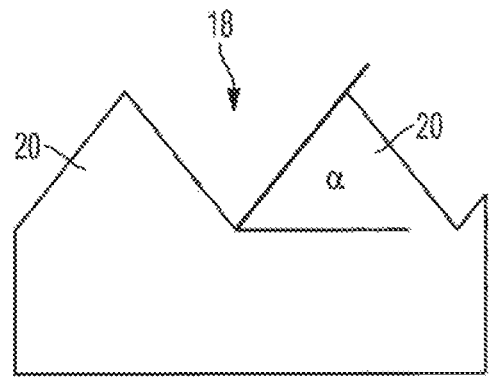
Figure 6C:
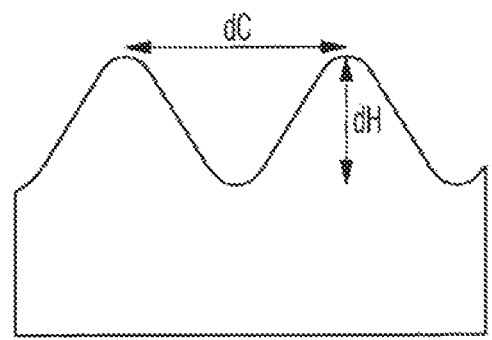

While FIG. 6A and FIG. 6C showing sinusoidal corrugations, according to FIG. 6B, triangular corrugation, in turn having the angle of inclination a may be seen. The angle, in large areas, may be adapted to the requirements. In the working example represented, it is 50 degrees, so that the aperture angle of the ribs is 80 degrees. Another exemplary magnitude is a=20 degrees, corresponding to an aperture angle of 140 degrees.

Figure 7:
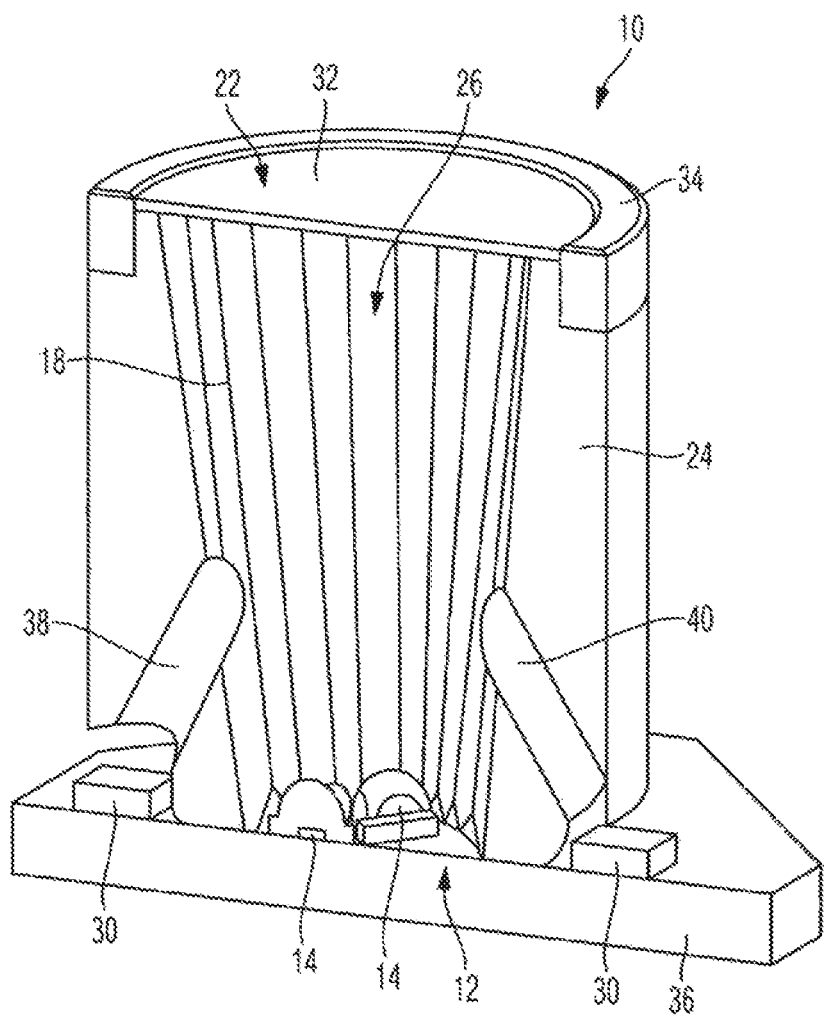
FIG. 7 is another embodiment of a homogeniser according to the invention in sectional representation.

From FIG. 7, another embodiment of the homogeniser may be seen. The wall 24 of the homogeniser 10 is solidly formed, and the homogeniser 10 is formed in two parts, wherein the cylindrical outside of the wall 24 is interrupted by respective retaining snaps, maintaining its basic cylindrical character.

The homogeniser 10, on the outside, is formed as a solid, especially essentially cylindrical body, having a wall thickness, which on the output side is at least a quarter, and on the input side is at least one third of the radius of the homogeniser (10).

In this embodiment, the homogeniser 10 simultaneously acts as a homogenisier and as an reflector, after coating a mirror layer onto the ribs 18 at the interior wall of the homogeniser 10 to form a reflector and after the reflector 26 conically enlarges towards the output surface 22.

The output surface 22, in this working example, is covered by a transparent cover plate 32, which is maintained with a holding ring 34 opposite of the homogeniser, and besides, is sealingly maintained.

A specific feature of the embodiment according to FIG. 7 is the integration of the sensors 30, which, together with the LED chips 14, are attached on a common base plate 36. The sensors 30 thus are located in the same plane as the LED chips 14.

From the interior space of the homogeniser 10 to the sensors 30 inclined sensor-light channels 38 and 40 extend, which due to their inclination, preferably capture the reflected light, for example the light reflected from a dental surface, and supplying it to the sensor 30.

The angle of inclination may for example be 30 degrees, in relation to the optical axis of the homogeniser 10, but may also be only 15 or for example also 40 degrees.

The sensor light channel 38 and 40 each terminates significantly spaced apart from the sensor 30. Thus, thermal separation is assured. The entire component of homogeniser and base plate is accommodated in a closed housing, so that the light provided via the sensor light channels is the only light that may reach the region of the sensor 30.

In this embodiment, the homogeniser according to the invention 10 has triple function. It serves as a reflector, due to the corrugation comprising the ribs 18 as a light mixer, and simultaneously serves as a feeding element for the sensor light.

The invention claimed is:

1. A homogenizer comprising
an input surface and
an output surface,
wherein the input surface and the output surface are incongruent to each other,
wherein between the input surface (12) and the output surface (22) at least an inclined surface extends, comprising a corrugation (18),
wherein the homogenizer (10) is formed as an internally reflecting hollow element,
wherein LED chips (14) are accommodated in the homogenizer (10), and
wherein the homogenizer (10) has sensor light channels (38, 40), extending between the interior space of the hollow element and a region outside the hollow element, extending in the plane of the LED chips (14).

2. The homogenizer according to claim 1,
wherein the input surface (12) is formed polygonally, and/or
wherein the output surface (22) is round.

3. The homogenizer according to claim 2,
wherein formed polygonally comprises squared or rectangularly and
wherein round comprises formed circularly.

4. The homogenizer according to claim 1,
wherein a plurality of LED chips (14) is arranged adjacent to the input surface (12), the LED chips each being cast with collecting lenses, wherein the LED chips (14) are completely accommodated in the reflector.

5. The homogenizer according to claim 1,
wherein the homogenizer (10), as a hollow element, extends to a base plate (36), to which the LED chips are attached.

6. The homogenizer claim 1,
wherein the output surface (22) is closed with a transparent cover plate,
wherein the transparent cover plate is inserted into the homogenizer (10) and, at a wall (24) of the homogenizer facing the output surface (22), the transparent cover plate is circumferentially bonded to the homogenizer (10) with a transparent adhesive,
wherein the transparent cover plate is bluntly positioned onto the output surface (22) of the homogenizer (10) and is fixed thereto.

7. The homogenizer according to claim 1,
wherein on the outside of the homogenizer (10), a solid, cylindrical body is formed having a wall thickness, which, at the output side, is at least a quarter of a radius of the homogenizer, and on the input side is at least one third of the radius of the homogenizer (10) on the outside.

8. The homogenizer according to claim 1,
wherein the sensor light channels (38, 40) extend to the sensors (30), and therefrom extend obliquely radially inwardly to the output surface (22) of the homogenizer.

9. The homogenizer according to claim 1,
wherein the corrugation (18) comprises a multitude of ribs (20), which extend across the inner circumference of the homogenizer (10).

10. The homogenizer according to claim 9,
wherein the multitude of ribs (20) comprise a number from 10 to 100.

11. The homogenizer according to claim 10,
wherein the multitude of ribs (20) comprise 20.

12. The homogenizer according to claim 1,
wherein ribs (20) of the corrugation (18) extend with a constant shape between the input surface (12) and the output surface (22) and/or
wherein the ribs (20) of the corrugation (18) are arranged in a regular pattern, in the same distance to one another.

13. The homogenizer according to claim 1,
wherein ribs (20) of the corrugation (18) extend parallel to each other, but with different shapes and/or
wherein the shape of the corrugation (18), is adapted to the light wavelength or the wavelength regions transmitted by the homogenizer (10).

14. The homogenizer according to claim 13,
wherein the shape of the ribs (20) is adapted to the light wavelength or the wavelength regions transmitted by the homogenizer (10).

15. The homogenizer according to claim 1,
wherein the corrugation (18) of the homogenizer (10) comprises a reflective layer.

16. The homogenizer according to claim 15,
wherein the reflective layer comprises a vapor-deposited reflective layer.

17. The homogenizer according to claim 1,
wherein the output surface (22) of the homogenizer (10) is adjacent to an input terminal of an optical fiber and wherein output and input terminal surfaces are aligned with each other.

18. The homogenizer according to claim 1,
wherein the homogenizer is formed in multiple parts, and
wherein the parts of the homogenizer (10) are especially maintained to one another by snap-in connections.

19. A light curing apparatus having an homogenizer comprising,
an input surface and
an output surface,
wherein the input surface and the output surface are incongruent to each other,
wherein between the input surface (12) and the output surface (22) at least an inclined surface extends, comprising a corrugation (18),
wherein the homogenizer (10) is formed as an internally reflecting hollow element,
wherein LED chips (14) are accommodated in the homogenizer (10),
wherein the homogenizer (10) is formed as a main reflector of the light curing apparatus and is located downstream of an optical path of a light source, and is located upstream of a light guide rod.

* * * * *